United States Patent [19]

Jacobson et al.

[11] 4,008,174

[45] Feb. 15, 1977

[54] PROCESS FOR REGENERATING A SOLID COPPER-CHROMIUM REACTANT USED IN THE REMOVAL OF HYDROGEN SULFIDE FROM HYDROGEN RECYCLE GAS

[75] Inventors: Robert L. Jacobson, Pinole; Kirk R. Gibson, El Cerrito, both of Calif.

[73] Assignee: Chevron Research Company, San Francisco, Calif.

[22] Filed: Jan. 19, 1976

[21] Appl. No.: 650,476

Related U.S. Application Data

[63] Continuation-in-part of Ser. No. 480,071, June 17, 1974, abandoned.

[52] U.S. Cl. .......................... 252/411 S; 208/138; 252/419; 423/230; 423/648
[51] Int. Cl.² ..................... B01J 23/92; B01J 23/94
[58] Field of Search ........... 252/411 S, 411 R, 416, 252/419; 423/230, 648; 55/73, 74; 208/140, 138

[56] References Cited

UNITED STATES PATENTS

| | | | |
|---|---|---|---|
| 1,947,776 | 2/1934 | Huff | 423/230 |
| 2,747,968 | 5/1956 | Pigache | 423/230 |
| 3,576,596 | 4/1971 | Kraml et al. | 252/476 |
| 3,778,501 | 12/1973 | Lang et al. | 252/411 S |
| 3,883,637 | 5/1975 | Benedict | 423/230 |

Primary Examiner—Winston A. Douglas
Assistant Examiner—P. E. Konopka
Attorney, Agent, or Firm—G. F. Magdeburger; R. H. Davies; W. D. Reese

[57] ABSTRACT

A process is disclosed for regenerating a solid reactant comprising a copper component and a chromium component disposed on a porous carbon support when the reactant has been expended by reaction with hydrogen sulfide contained in hydrogen recycle gas in a hydrocarbon reforming system, regeneration being accomplished by: (a) contacting the expended solid reactant with dilute oxygen in an inert diluent gas at a temperature in the range from 200° to 425° F; (b) contacting the solid material from step (a) with hydrogen at a temperature in the range from 300° to 500° F; and (c) contacting the solid material resulting from step (b) with an inert gas at a temperature in the range from 400° to 600° F.

5 Claims, No Drawings

PROCESS FOR REGENERATING A SOLID COPPER-CHROMIUM REACTANT USED IN THE REMOVAL OF HYDROGEN SULFIDE FROM HYDROGEN RECYCLE GAS

CROSS-REFERENCE TO RELATED APPLICATION

This application is a continuation-in-part of our co-pending application Ser. No. 480,071, filed June 17, 1974, and now abandoned, the teachings of which are incorporated herein by specific reference.

BACKGROUND

The desirability of removing sulfur compounds from gaseous streams for various reasons has been long recognized. Activated carbon has often been used to remove sulfur compounds such as $H_2S$ from natural and manufactured gases, ammonia, hydrogen and LPG. Recently it has become desirable to remove substantially all sulfur compounds from the hydrogen recycle stream used in hydrocarbon reforming systems. Modern bimetallic reforming catalysts require low-sulfur conditions for efficient operation.

This invention is directed to regenerating a solid reactant of copper-chromium on a high-surface-area carbon support, when the reactive sulfur removal capacity of the reactant has been used up by reaction with hydrogen sulfide. The invention affords a substantially complete regeneration of the solid reactant and, at the same time, induces little or no change to the porous carbon support from oxidation or sintering. This invention has particular utility in regenerating solid reactants which have become expended in removing hydrogen sulfide from recycle hydrogen in reforming systems in which very low recycle hydrogen gas sulfur levels (as low as tenths of a ppm) are desired, allowing the regenerated reactant to be reused in scrubbing sulfur compounds from the recycle hydrogen stream.

A number of processes have been disclosed for removing sulfur compounds from gaseous streams. U.S. Pat. No. 3,382,044 teaches the use of zinc oxide to adsorb hydrogen sulfide. U.S. Pat. No. 3,398,509 teaches the use of carbon to adsorb $SO_2$ and heating the carbon in an inert gas to desorb the $SO_2$. U.S. Pat. No. 3,416,293 teaches removing the sulfur compounds from industrial gas streams by adsorption on a bed of activated carbon modified by the addition of a metal selected from copper, iron, manganese, nickel, cobalt, cadmium and zinc, and a process for regenerating the adsorbent with steam.

U.S. Pat. No. 3,501,897 teaches a cyclic regenerative process for removing sulfur oxides from flue gas by means of a solid acceptor which may be copper oxide, wherein the regeneration of the solid acceptor is carried out by passing a reducing gas through it at a temperature from about 300°–500° C. The base material must be capable of withstanding the temperatures used for the removal of the sulfur oxides. Suitable materials are alumina, silica, silica-alumina, and/or silica-magnesia.

Pages 66–70 of the Aug. 31, 1972 Oil & Gas Journal discuss the regeneration of a copper oxide adsorbent used for scrubbing $SO_2$.

U.S. Pat. No. 3,739,550 teaches regeneration of carbonaceous adsorbents containing vanadium, lithium, aluminum or chromium and phosphorus with nitrogen at 600° C.

U.S. Pat. No. 2,747,968 describes regeneration of a copper, nickel or cadmium component which may be supported on a carrier such as alumina or silica and may be promoted with chromic acid, nickel oxide or nickel sulfide. Regeneration is effected at 350°–850° C (about 660°–1560° F) by first passing a slow stream of an oxidizing gas such as air over the reactant followed by a slow stream of a reducing gas, after the reactant has become expended by contact with hydrogen sulfide-containing gases.

U.S. Pat. No. 1,947,776 describes regeneration of a reactant containing, e.g., copper and chromium on, e.g., pumice or firebrick, by passing air over the reactant at an elevated temperature, e.g., 840° F.

U.S. Pat. No. 3,576,596 describes removal of carbon monoxide and nitric oxide from gases using a mixture of copper and chromium on activated carbon.

U.S. Pat. No. 3,883,637 describes removing odorous sulfur compounds from air using a mixture of copper and chromium on activated charcoal.

The process of the present invention provides an effective way of regenerating a solid reactant which has become expended by reaction with hydrogen sulfide in a hydrogen recycle gas stream when the reactant is comprised in part of porous carbon, in a manner which prevents sintering or oxidation and concomitant destruction of the reactant and also allows the reactant to be reused for removing sulfur from the hydrogen recycle gas to provide a substantially sulfur-free recycle stream.

SUMMARY

In an embodiment, the present invention relates to a process for regenerating a solid reactant comprising a copper component and a chromium component disposed on a high-surface-area carbon support, the reactant having reacted to form a sulfur compound by contact with a hydrogen sulfide-containing recycle hydrogen stream in a hydrocarbon reforming system for removing substantially all the hydrogen sulfide from the hydrogen stream, the regeneration process comprising the steps of: (a) contacting the sulfur compound-containing reactant with an oxygen-containing gas comprising an inert gas and about 0.1 to about 2 weight percent oxygen to oxidize the sulfur compound, the contacting being performed at a temperature of about 200° F to about 425° F, whereby reduction of the surface area of the carbon support is prevented, and removing the resulting gas from contact with the resulting solid; (b) contacting the resulting solid from step (a) with a gas comprising hydrogen at a temperature of about 300° F to about 500° F to convert sulfur remaining in the resulting solid to sulfur dioxide, a portion of the sulfur dioxide being adsorbed on the solid, and removing the resulting gas from contact with the resulting solid; and (c) contacting the resulting solid from step (b) with an inert gas at a temperature of 450° F to 600° F, and removing the resulting gas from contact with the resulting solid, whereby adsorbed sulfur dioxide is removed from the solid.

By the process of this invention, regeneration of a solid reactant, comprised in part of a porous carbon support subject to destructive sintering or oxidation can be carried out in an expeditious and practical manner.

DETAILED DESCRIPTION

The solid reactant which is regenerated by the process of the present invention includes a reactive mixture of copper and chromium and/or compounds thereof disposed on a porous carbon support.

The metal or metal compounds, or mixtures thereof, are deposited on a high-surface-area carbon. The porous carbon support serves a dual function: (1) it supplies an inexpensive, physically rugged support with sufficient mechanical strength to sustain the weight of the fixed bed regardless of occasional surges in the gas flow; and (2) it spreads out the reactive metals, providing an increased surface area of active reactant to the hydrogen recycle gas to be purified. The high surface area facilitates reaction with hydrogen sulfide in the hydrogen recycle gas under conditions dictated by the hydrocarbon reforming system, such as the recycle gas temperature and pressure. It permits the retention of large amounts of sulfur per unit weight of metals before the reactive capacity of the metals is exhausted.

By a high-surface-area carbon support, we mean a microporous material with an area of at least 50 m$^2$ per gram, preferably 100 to 1,000 and as high as 1,200 m$^2$ per gram. The reactive copper-chromium mixture, present in the form of, e.g., metal oxides, may be incorporated into the support by known methods, including impregnation from solutions onto the preformed porous carbon support, as by co-impregnation from a single solution or sequential impregnation.

The weight percent of reactive copper and chromium metal component present in the solid reactant may vary widely. High metal contents provide a large reservoir for accepting as much sulfur as possible. If the metals content is too high, however, the effectiveness per unit weight of metal decreases, and may approach the case of the unsupported metal oxides. Effective ranges for the total combined reactive copper and chromium contents are from 3 to 30% by weight, preferably from 20 to 30%. We have used successfully, inter alia, desulfurizing beds, comprising 7.8%–16% copper and 1.75%–4% chromium on activated carbon. The percentages given are for the elemental metals, although the metals may also be present in the reactant as the oxides initially and in mixtures containing the oxides and sulfides after the solid reactant has been used.

Conditions under which the purification of the hydrogen recycle gas stream containing hydrogen sulfide is carried out are basically determined by the conventional conditions required in the hydrocarbon reforming system in which the hydrogen stream is used. When recycle hydrogen gas is being purified of hydrogen sulfide for use in a reforming system, the pressure is generally in the range of 50 to 1000 psig. When the reforming system employs a platinum catalyst containing a promoter such as rhenium, the hydrogen recycle gas pressure is normally in the lower end of this range, e.g., about 50 to 500 psig. The temperature used during the recycle gas purification operation also depends on the temperature required by the hydrocarbon reforming system, e.g., a 100°–200° F recycle gas temperature is normal.

The solid reactant accepts sulfur from the hydrogen recycle gas stream, forming solid sulfur compounds such as copper sulfide. Sulfur normally enters the reforming system in small amounts in the hydrocarbon feed. The reaction of hydrogen sulfide contained in the hydrogen recycle gas with the metal oxides is rapid enough so that the length of time of contact between the solid reactant and hydrogen recycle gas is not critical. As a rule of thumb, for the purification of a hydrogen recycle stream being used in a hydrocarbon reforming system, the volume of the reactant bed is equivalent to about 15% of the volume of the bed of reforming catalyst used in the system.

Ordinarily, the hydrogen recycle gas cleansing or purification bed is positioned at the point where the recycled hydrogen gas is discharged from the recycle gas compressor. Operation for scrubbing hydrogen sulfide from the hydrogen recycle gas is preferably continued until analysis shows an undesirably high sulfur content in the hydrogen leaving the purification bed. In normal operation, substantially all hydrogen sulfide is removed from the reformer hydrogen recycle stream, i.e., the sulfur content of the treated hydrogen is less than 1 ppm and preferably less than 0.5 ppm. When this sulfur level is exceeded, the reactant bed is taken off stream, the solid reactant is regenerated according to the process of the present invention, and the reactant is then returned to scrubbing service.

The present regeneration process includes the steps of:

a. contacting an expended, sulfur compound-containing reactant with an oxygen-containing gas comprising an inert gas having about 0.1 to about 2 weight percent oxygen therein to oxidize the sulfur compound, the contacting being performed at a temperature of about 200° F to about 425° F, whereby reduction of the surface area of the carbon support is prevented, and removing the resulting gas from contact with the resulting solid;

b. contacting the resulting solid from step (a) with a gas comprising hydrogen at a temperature of about 300° F to about 500° F to convert sulfur remaining in the solid to sulfur dioxide, a portion of the sulfur dioxide being absorbed on the solid, and removing the resulting gas from contact with the resulting solid; and c. contacting the resulting solid from step (b) with an inert gas at a temperature of 450° F to 600° F, and removing the resulting gas from contact with the resulting solid, whereby adsorbed sulfur dioxide is removed from the solid.

Step (c) is essential in that it removes SO$_2$ adsorbed in the solid reactant, particularly in the carbon support, before the regenerated solid reactant is placed back in hydrogen recycle gas scrubbing service. If even a relatively small amount of SO$_2$ remains in the solid reactant, it will be converted back to H$_2$S during use of the hydrogen gas stream in hydrocarbon reforming, leading to lowered reforming catalyst activity because of the presence of sulfur in the catalyst bed.

Before contacting the expended solid reactant with a dilute oxygen stream, the expended bed of solid reactant is preferably swept free from hydrogen recycle gas with a stream of an inert gas, e.g., nitrogen, to avoid combining heated oxygen and hydrogen. Each of the regeneration steps of the process is preferably carried out by passing a stream of the contacting gas through the bed of solid reactant and out of the system to remove undesirable gaseous sulfur compounds as they are released from the solid.

The amount of oxygen present in the inert diluent gas in step (a) is in the range from 0.1 to 2.0%, preferably 0.3 to 1.0%. The inert diluent gas is preferably nitrogen and/or steam, although any gas which does not appreciably react with the oxygen or the solid reactant under the temperature and pressure employed in step (a) may be used. For example, argon, helium, etc., may also be used. The inert diluent gas usually contains steam, which can conveniently be used to provide the necessary regeneration temperature in the bed of solid reactant.

The oxidation step of the process is carried out at a temperature of 200°–425° F in the presence of a controlled dilute amount of oxygen, so that the high surface area of the solid reactant will not be reduced. Reduction of the surface area of the reactant is undesirable in that this results in a loss of the sulfur-accepting capacity of the reactant. Surface area reduction is prevented in the present regeneration process both by the use of dilute oxygen (less than 2% weight) in an inert gas, as well as by employing a mild oxidation temperature (below 425° F). The use of either excessively high temperatures, high-oxygen-content gases (e.g., air), or both, would have a deleterious effect on the reactant. A temperature between 350° F and 400° F, especially about 375° F, is preferred.

The oxidation step oxidizes sulfur in the reactant to form solid compounds containing the reactive metals, sulfur and oxygen, e.g., copper sulfate. Accordingly, there is a net uptake of oxygen into the solid reactant, with release of only a small amount of gaseous sulfur compounds, such as sulfur dioxide. Preferably the oxidation step is continued until there is little or no loss of oxygen from the dilute oxygen gas during its passage through the reactant bed, indicating substantially complete oxidation of sulfur in the solid reactant. Oxygen loss can conveniently be determined by analysis of the oxygen-containing gas before and after it is contacted with the solid reactant. When analysis indicates little or no oxygen loss, the flow of oxidizing gas is discontinued, the solid reactant bed is purged of oxygen, and the second step of regeneration is begun. The oxidation step is normally complete after about 3 hours when a temperature of 375° F is employed. The exact time depends on the temperature, pressure, solid reactant composition, etc., and is not critical. Further, the oxidation step need not be carried to completion, if it is not desired to do so, prior to commencing the second, hydrogen treatment step of regeneration. Incomplete oxidation will, of course, somewhat reduce the subsequent sulfur-accepting capacity of the solid reactant when it is returned to sulfur-removal use.

The hydrogen-containing gas employed in step (b) of the regeneration process may include mixtures of hydrogen with inert gases such as nitrogen, steam, etc. The amount of the hydrogen gas is not critical (between about 1 volume percent and about 5 volume percent). A mixture of about 2 volume percent hydrogen in nitrogen, for example, has been found to give good results. The second, hydrogen treatment step is carried out at a temperature of 300°–500° F. A temperature between 350° F and 400° F, especially about 375° F, is preferred.

The hydrogen treatment step converts sulfur compounds in the solid reactant, e.g., metal sulfates, to gaseous sulfur compounds, particularly sulfur dioxide and hydrogen sulfide. Accordingly, there is a net consumption of uncombined hydrogen gas during the hydrogen treatment. Preferably the hydrogen treatment step is continued until there is little or no evidence of hydrogen consumption from the hydrogen-containing gas, indicating substantially complete reaction of sulfur compounds, such as sulfate, in the solid reactant to form gaseous sulfur dioxide and hydrogen sulfide. Hydrogen loss from the hydrogen-containing gas can conveniently be determined by analysis of the hydrogen content of the hydrogen-containing gas before and after it is contacted with the solid reactant. When analysis indicates little or no hydrogen consumption, the flow of hydrogen-containing gas through the solid reactant bed is discontinued, the reactant bed is purged of hydrogen, and the third step of regeneration is begun. The hydrogen treatment step is normally complete after about 3 hours when a regeneration temperature of 375° F is employed. The exact time depends on the temperature, pressure, solid reactant composition, etc., and is not critical. Unlike the oxidation step, the hydrogen treatment step should be carried substantially to completion, as evidenced by little or no further hydrogen consumption, to prevent sulfur contamination of the reformer hydrogen recycle gas when the solid reactant is returned to use in recycle gas scrubbing.

Treatment with the hydrogen-containing gas is sufficient to remove substantially all nonadsorbed sulfur dioxide and hydrogen sulfide from the solid reactant, these gaseous sulfur compounds being withdrawn from the solid reactant bed as part of the stream of gas resulting from the hydrogen treatment. A portion of the gaseous sulfur compounds, however, remain adsorbed in the solid reactant after substantial completion of the hydrogen treatment, and these would be desorbed slowly, so that their removal from the solid reactant by continuation of the hydrogen gas treatment is impracticable. It is therefore essential to remove the adsorbed gaseous sulfur compounds from the solid reactant by the third regeneration step of the present process in order to prevent the subsequent slow desorption of the adsorbed sulfur gases into the reformer hydrogen recycle gas when the solid reactant is returned to use in recycle gas treatment. If not thus removed, sulfur dioxide can be slowly desorbed, e.g., at a rate of less than 10 ppm sulfur in reformer hydrogen recycle gas. Sulfur present in such a concentration adversely affects the reforming catalyst. Further, slow desorption of sulfur by the reformer recycle gas can continue for long periods of reforming operation, e.g., 100 hours or more.

The inert gas employed in step (c) can be any gas, or mixture of gases, which is not reactive with the solid reactant at the conditions encountered in step (c). For example, nitrogen, steam, argon, helium, etc., can be used. Nitrogen is preferred. The inert gas stream advantageously includes steam, which may be used to heat the inert gas stream and solid reactant to the desired regeneration temperature.

The third, inert gas treatment step of the process is carried out at a temperature of 450°–600° F. A temperature of about 450° F to 550° F, especially about 500° F, is preferred. The inert gas treatment step removes adsorbed gaseous sulfur compounds, particularly sulfur dioxide and hydrogen sulfide, from the solid reactant. Without the use of the inert gas treatment, such adsorbed gaseous sulfur compounds would eventually be desorbed from the reactant during recycle gas scrubbing operations, and would thereby adversely affect the reforming catalyst. Accordingly, the inert gas treatment step is continued until there is little or no sulfur, i.e., less than about 10 ppm, in the inert gas when it is withdrawn from contact with the solid reactant. Preferably, the inert gas treatment is continued until analysis of the stream of inert gas exiting the solid reactant bed shows less than 5 ppm sulfur dioxide. The inert gas treatment is then discontinued, and the temperature and pressure in the bed of regenerated solid reactant are adjusted as desired for use in scrubbing hydrogen recycle gas in the reforming system, and the solid reactant is returned to sulfur-acceptance operation. The inert gas treatment step is normally complete in about 3 to 10 hours when a temperature of about 500° F is employed. The exact time required depends on the temperature, pressure, solid reactant composition, etc.

Atmospheric pressure may be used in each of the three steps in the regeneration process, although low superatmospheric pressures are preferred, e.g., 30–100 psia, especially about 60 psia.

The present invention is further illustrated by the following example, which does not constitute a limitation on the scope of the invention.

EXAMPLE

In each cycle, a 100-cc bed of a solid reactant containing 14% by weight Cu and 4% by weight Cr (on an elemental-metal basis) supported on activated carbon which had a surface area prior to incorporation of the Cu-Cr in excess of 1,000 m$^2$/gram was first employed to remove $H_2S$ from an $H_2S$- and HCL-containing $H_2$ gas. Sulfur removal operating conditions were 200 psig, 200° F, and about 6 SCF/hr gas flow rate. The entering $H_2$-rich gas stream contained 50 ppm $H_2S$, 30 ppm HCl and 50 ppm $H_2O$. The hydrogen gas was substantially completely freed from $H_2S$ by the solid reactant during each scrubbing cycle until the reactant had accumulated about 1.5% by weight sulfur. Seven cycles of sulfur removal and reactant regeneration were carried out. After each sulfur removal period, when the solid reactant had become expended, the solid reactant bed was regenerated as follows:

a. The bed was contacted with a dilute oxygen-containing gas at 375° F and a pressure of 60 psia for about 3 hours. The oxidizing gas stream was a mixture of 1% volume $O_2$ in $N_2$-steam inert diluent. The $SO_2$ content of the exiting non-condensable oxidizing gas stream was found to be less than 400 ppm $SO_2$, indicating very little sulfur removal.

b. A gas stream containing about 2% volume $H_2$ in $N_2$-steam inert diluent was then introduced at 375° F at a rate of about 7 liters/hour and a pressure of 60 psia. During the reduction step, $SO_2$ levels of 15,000 ppm in the exiting gas stream were observed.

c. The flow of the hydrogen-containing gas was discontinued after 3 hours and an inert gas stream containing steam and $N_2$ was then passed through the bed. The temperature of the bed was increased to 500° F, resulting in further removal of $SO_2$ from the bed of reactant. When the solid reactant bed was returned to use in removing $H_2S$ from the hydrogen stream, no detectable $SO_2$ was observed in the hydrogen effluent from the bed.

When the third step of the regeneration process, using the higher-temperature inert gas stream to remove adsorbed $SO_2$, was eliminated, 7–15 ppm $SO_2$ was observed in the effluent gas during subsequent $H_2S$ removal operations, i.e., sufficient hydrogen recycle sulfur content to adversely affect hydrocarbon reforming operations with a modern bimetallic catalyst.

What is claimed is:

1. A process for regenerating a solid reactant comprising copper and chromium disposed on a high-surface-area carbon support, said reactant having reacted to form a solid sulfur compound by contact with a hydrogen sulfide-containing recycle hydrogen stream in a hydrocarbon reforming system for removing substantially all the hydrogen sulfide from said hydrogen stream, said regeneration process comprising the steps of:

a. forming sulfate by reacting said sulfur compound with oxygen in an oxygen-containing gas comprising an inert gas and about 0.1 to about 2 weight percent oxygen at a temperature between about 200° F and 425° F, whereby reduction of the surface area of said carbon support is prevented, and removing the resulting gas from contact with the resulting solid;

b. forming sulfur dioxide by reacting said sulfate with hydrogen at a temperature of about 300° F to about 500° F, whereby a portion of the sulfur dioxide is adsorbed on said resulting solid, and removing the resulting gas from contact with said resulting solid; and c. desorbing sulfur dioxide from said resulting solid by contacting said solid with an inert gas at a temperature of 450° F to 600° F and removing the resulting gas from contact with said solid.

2. A process according to claim 1 wherein said expended reactant is contacted with said oxygen-containing gas at a temperature between 350° F and 400° F.

3. A process according to claim 1 wherein said resulting solid from step (a) is contacted with hydrogen at a temperature between 350° F and 400° F.

4. A process according to claim 1 wherein said resulting solid from step (b) is contacted with an inert gas at a temperature between 450° F and 550° F.

5. A process according to claim 1 wherein said solid reactant contains between 7.8 and 16 weight percent of said copper component and between 1.7 and 4 weight percent of said chromium component, on an elemental-metal basis.

* * * * *